(12) United States Patent
Staszak et al.

(10) Patent No.: US 9,314,187 B2
(45) Date of Patent: Apr. 19, 2016

(54) BICYCLE SEAT SIZER AND POSITIONING DEVICE

(75) Inventors: Jeffrey R. Staszak, Deerfield, WI (US); Michael L. Leighton, Watertown, WI (US); Allen Hu, Taichung (TW)

(73) Assignee: Trek Bicycle Corporation, Waterloo, WI (US)

( * ) Notice: Subject to any disclaimer, the term of this patent is extended or adjusted under 35 U.S.C. 154(b) by 2153 days.

(21) Appl. No.: 11/938,360

(22) Filed: Nov. 12, 2007

(65) Prior Publication Data
US 2009/0124935 A1 May 14, 2009

(51) Int. Cl.
*A61B 5/107* (2006.01)
*B62J 1/00* (2006.01)
*A61B 5/00* (2006.01)

(52) U.S. Cl.
CPC ............... *A61B 5/107* (2013.01); *B62J 1/007* (2013.01); *A61B 5/1077* (2013.01); *A61B 5/6892* (2013.01)

(58) Field of Classification Search
CPC .. A61B 5/1077; A61B 5/1078; A61B 5/6894; A61B 5/6895
USPC ............ 600/587, 594, 595, 592; 33/511, 512, 33/514.2, 515
See application file for complete search history.

(56) References Cited

U.S. PATENT DOCUMENTS

| | | | |
|---|---|---|---|
| 570,497 A | 11/1896 | Pattisson | |
| 593,331 A | 11/1897 | Noirit | |
| 603,943 A | 5/1898 | Clifford | |
| 604,347 A | 5/1898 | Bray | |
| 606,818 A | 7/1898 | Best | |
| 608,682 A | 8/1898 | Jamieson | |
| 619,768 A | 2/1899 | Lewis, Jr. | |
| 629,956 A | 8/1899 | Craig | |
| 633,487 A | 9/1899 | Radermacher | |
| 656,854 A | 8/1900 | Nord | |
| 1,830,648 A | 11/1931 | Engel | |
| 2,162,916 A | 6/1939 | Hyland | |
| 2,378,039 A | 6/1945 | Schenker | |
| 2,942,344 A * | 6/1960 | Brannock | 33/3 B |
| 3,264,382 A | 8/1966 | Angell et al. | |
| 3,458,898 A | 8/1969 | Casparis | |
| 3,830,896 A | 8/1974 | Flicer et al. | |
| 3,844,611 A | 10/1974 | Young | |
| 3,857,188 A * | 12/1974 | Foster et al. | 33/388 |

(Continued)

FOREIGN PATENT DOCUMENTS

| | | |
|---|---|---|
| DE | 94202 | 8/1896 |
| DE | 106430 | 11/1899 |

(Continued)

OTHER PUBLICATIONS

English Translation of EP 1698545 A1.*

*Primary Examiner* — Adam J Eiseman (57) ABSTRACT

A device for determining the distance between protruding anatomical features of a user includes a first portion having a volume of displaceable material and a second portion having at least one scale attached thereto. The displaceable material is configured to be displaced when subjected to a pressured loading to create depressions in the displaceable material. The second portion is movable relative to the first portion such that the scale can be aligned with the depressions to provide an indication of the distance therebetween. Preferably, the scale is coded for association of the distance with a desired bicycle seat size.

25 Claims, 5 Drawing Sheets

(56) References Cited

U.S. PATENT DOCUMENTS

| | | |
|---|---|---|
| 4,046,611 A | 9/1977 | Sanson |
| 4,089,559 A | 5/1978 | Prange et al. |
| 4,136,506 A | 1/1979 | Miller |
| 4,347,213 A | 8/1982 | Rogers, Jr. |
| 4,387,925 A | 6/1983 | Barker et al. |
| 4,413,540 A | 11/1983 | Burge |
| 4,429,915 A | 2/1984 | Flager |
| 4,454,090 A | 6/1984 | Saumell |
| 4,470,782 A | 9/1984 | Zimmerman, Jr. et al. |
| 4,493,877 A | 1/1985 | Burnett |
| 4,512,608 A | 4/1985 | Erani |
| 4,525,130 A | 6/1985 | Netznik |
| 4,541,668 A | 9/1985 | Rouw |
| 4,615,856 A | 10/1986 | Silverman |
| 4,637,789 A | 1/1987 | Netznik |
| 4,669,255 A | 6/1987 | Wicks |
| 4,683,709 A | 8/1987 | Vasko et al. |
| 4,697,240 A | 9/1987 | Cedar et al. |
| 4,728,150 A | 3/1988 | Gaudreau, Jr. |
| 4,827,701 A | 5/1989 | Gonzales |
| 4,867,922 A | 9/1989 | Zuccato |
| 4,876,758 A | 10/1989 | Rolloff et al. |
| 4,877,286 A | 10/1989 | Hobson et al. |
| 4,890,235 A | 12/1989 | Reger et al. |
| 4,993,429 A | 2/1991 | Krinsky |
| 4,998,354 A | 3/1991 | Silverman et al. |
| 5,027,589 A | 7/1991 | Gleb et al. |
| 5,058,367 A | 10/1991 | Evertson |
| 5,060,393 A | 10/1991 | Silverman et al. |
| 5,119,618 A | 6/1992 | Streck |
| 5,123,698 A | 6/1992 | Hodges |
| 5,175,986 A | 1/1993 | Farley |
| 5,203,607 A | 4/1993 | Landi |
| 5,252,373 A | 10/1993 | Ganske et al. |
| 5,330,249 A | 7/1994 | Weber et al. |
| 5,351,408 A | 10/1994 | Street |
| 5,352,016 A | 10/1994 | Hobson |
| 5,375,397 A | 12/1994 | Ferrand et al. |
| 5,385,155 A | 1/1995 | Kittelsen et al. |
| 5,387,025 A | 2/1995 | Denisar |
| 5,470,590 A | 11/1995 | Brubaker et al. |
| 5,558,395 A | 9/1996 | Huang |
| 5,577,372 A | 11/1996 | Gronberg |
| 5,709,430 A | 1/1998 | Peters |
| 5,725,274 A | 3/1998 | Bergmeister |
| 5,765,912 A | 6/1998 | Bontrager |
| 5,782,070 A | 7/1998 | Knight et al. |
| 5,787,692 A | 8/1998 | Purdy |
| 5,802,823 A | 9/1998 | Woods |
| 5,823,618 A | 10/1998 | Fox et al. |
| 5,873,626 A | 2/1999 | Katz |
| 5,911,474 A | 6/1999 | Lee |
| 5,918,931 A | 7/1999 | Culbertson |
| 5,988,740 A | 11/1999 | Caraballo |
| 6,039,395 A | 3/2000 | Culbertson |
| 6,050,067 A | 4/2000 | Knight et al. |
| 6,059,359 A | 5/2000 | Cassani |
| 6,068,333 A | 5/2000 | Dixon |
| 6,106,059 A | 8/2000 | Minkow et al. |
| 6,139,097 A | 10/2000 | Yates |
| 6,139,098 A | 10/2000 | Carrillo |
| 6,161,238 A | 12/2000 | Graebe |
| 6,257,662 B1 | 7/2001 | Yates |
| 6,305,743 B1 | 10/2001 | Wheeler |
| 6,402,235 B1 | 6/2002 | Letendre |
| 6,402,236 B1 | 6/2002 | Yates |
| D469,703 S | 2/2003 | Stahl |
| 6,615,568 B1 | 9/2003 | Roskies |
| 6,625,897 B2 | 9/2003 | Tadin |
| 6,769,234 B2 | 8/2004 | Hadlock |
| 6,990,744 B2 | 1/2006 | Bieganek et al. |
| 7,022,275 B2 | 4/2006 | Bigolin |
| 7,044,540 B2 | 5/2006 | Bigolin |
| 7,044,542 B2 | 5/2006 | Muscat |
| 7,121,622 B1 | 10/2006 | Mendez |
| 7,284,336 B2 | 10/2007 | Bird et al. |
| 7,441,343 B2 | 10/2008 | Bird et al. |
| 7,448,141 B2 | 11/2008 | Bird et al. |
| 2002/0069464 A1 | 6/2002 | Welsh |
| 2002/0185897 A1 | 12/2002 | Crutch |
| 2004/0056519 A1 | 3/2004 | Kastariak |
| 2004/0232742 A1 | 11/2004 | Oehler |
| 2005/0212337 A1 | 9/2005 | Lee |
| 2006/0022496 A1 | 2/2006 | Fregonese et al. |
| 2006/0049675 A1 | 3/2006 | Fregonese et al. |
| 2006/0218809 A1* | 10/2006 | Bird et al. .................. 33/512 |
| 2007/0001336 A1 | 1/2007 | Nishibori et al. |
| 2007/0273185 A1 | 11/2007 | Bird et al. |
| 2008/0134533 A1 | 6/2008 | Bird et al. |
| 2008/0184491 A1* | 8/2008 | Kemper .................... 5/653 |

FOREIGN PATENT DOCUMENTS

| | | |
|---|---|---|
| DE | 19805802 | 8/1999 |
| EP | 1698545 A1 | 9/2006 |
| GB | 20112 | 1/1984 |
| GB | 2121740 | 1/1984 |
| WO | WO 95/25662 | 9/1995 |
| WO | WO 9717281 | 5/1997 |
| WO | WO 9829331 A1 | 7/1998 |
| WO | WO 01/34456 | 5/2001 |
| WO | WO 01/94192 | 12/2001 |
| WO | WO 03/011679 A1 | 2/2003 |
| WO | WO 2004/031025 | 4/2004 |
| WO | WO 2005/105558 | 11/2005 |
| WO | WO 2007/031943 | 3/2007 |

* cited by examiner

BICYCLE SEAT SIZER AND POSITIONING DEVICE

BACKGROUND OF THE INVENTION

The present invention relates generally to bicycles and, more particularly, to a device for associating a rider's anatomy with a preferred size of a bicycle seat and orienting the preferred seat relative to a bicycle.

Many bicycle seats are provided with a generally concave upper surface constructed to support a seated rider. Many riders suffer from adverse physical effects do to the interaction of the seat with rider anatomy. Particularly, during long rides, the extended duration of interaction of the rider with the seat compresses the rider's perineal area. This compression detrimentally affects rider circulation and can result in the sensation of numbness and/or rider discomfort. Although the discomfort can be common in both male and female riders, impotence can result from extended and repeated periods of the compression and/or circulation effects in male riders.

Having recognized the adverse physical interaction with the seat, others have provided seats with hollowed center cavities, raised perimeter areas, seats constructed of a variety of pliable or deformable materials, and/or combinations thereof. While these approaches somewhat abate most of the incidence of perineal compression, they also substantially increase the cost and complexity of the construction and assembly of such bicycle seats.

Others abate the problem of perineal compression by providing a variety of saddle sizes having a variety of upper surface contours such that a majority of the weight of the rider is supported by the ischial tuberosities of the rider's pelvis skeletal structure. One problem with such an approach is the accurate determination of the spacing between the ischial tuberosities such that a specific seat size and shape can be associated with the specific user. Commonly, riders would simply sit upon a number of seats for brief periods of weighted loading to determine which seat "felt best". Unfortunately, the effects of perineal compression commonly only become apparent after extended periods of engagement with a particular seat. Accordingly, such trial and error efforts often associate a rider with a less than desired seat size and shape.

Others have attempted to better associate a rider's physiology with a seat by measuring indentations that are formed by the rider sitting upon a deformable material such as foam or the like. Although such processes allow for closer association of the riders physiology with a desired seat construction, such size determining systems are susceptible to individual measurement variations. That is, a user may improperly measure the indentation spacing and thereby select a seat size and shape that is less than desirable. Additionally, such systems commonly include a one time use deformable material such that sufficient amounts of the material must be maintained on hand.

Therefore, there is a need for a reusable device that can quickly and accurately measure a skeletal feature and associate the size of the skeletal structure with a preferred bicycle seat size.

BRIEF DESCRIPTION OF THE INVENTION

An illustrative embodiment relates to a seat size determining device that overcomes one or more of the aforementioned drawbacks. One aspect of the invention is directed to a device for determining the distance between protruding anatomical features of a user. The device includes a first portion having a volume of displaceable material and a second portion having at least one scale attached thereto. The displaceable material is configured to be displaced when subjected to a pressured loading to create depressions in the displaceable material. The second portion is movable relative to the first portion such that the scale can be aligned with the depressions to provide an indication of the distance between the depressions. Preferably, the first and second portion bypass one another such that the scale can be viewed through the depressions formed in the displaceable material. It is also preferred that the scale is coded for association of the distance with a desired bicycle seat size.

Another illustrative embodiment relates to a seat sizer that includes a pliable material contained in a cavity of a first member. The cavity and pliable material are configured such that the pliable material is displaceable within the cavity. An indicator is connected to a second member that is movable relative to the first member. The indicator is configured to be visible through the cavity to indicate a lateral spacing of an anatomical feature.

Another illustrative embodiment relates to a saddle sizing device that has a first portion having an amount of a pliable material affixed thereto and a second portion that cooperates with the first portion to bypass the pliable material. The device includes a first indicator attached to the second portion and configured to correspond to an anatomical feature of a first class of user and a second indicator attached to the second portion and configured to correspond to an anatomical feature of a second class of user.

Another illustrative embodiment relates to a bicycle seat tool that includes a sizer having a measuring portion removably associated with a scale portion. A volume of deformable material is attached to the measuring portion and is displaceable when subjected to loading. A first scale is attached to the scale portion and has a generally centrally oriented origin. An inclination indicator is secured to one of the measuring portion and the scale portion. Such a seat tool provides a multifunctional tool for configuring a bicycle to an intended user.

Another illustrative embodiment relates to providing a seat sizer tool or device in accordance with one or more of the above aspects and wherein one portion of the seat sizer tool is provided in the shape of a seat, stool, or bench. Preferably, the scale is attached to the bench and the container of pliable material is movable relative thereto.

Another illustrative embodiment relates to providing more than one scale such that multiple classes of users can utilize the device. For example, it is envisioned that the device include one scale that is calibrated to a range of sizes of a male anatomical feature and a second scale that is calibrated to a range of sizes of the anatomical feature of women. Such a configuration further enhances the functionality as well as the ease of use of the tool.

The illustrative embodiments summarized above are not limited to any one particular embodiment of the invention. That is, many or all of the aspects above may be achieved with any particular embodiment of the invention. Those skilled in the art will appreciate that the invention may be embodied in a manner preferential to one aspect or group of aspects and advantages as taught herein. These and various other aspects, features, and advantages of the present invention will be made apparent from the following detailed description and the drawings.

DETAILED DESCRIPTION OF THE PREFERRED EMBODIMENT

Figures 1, 2:
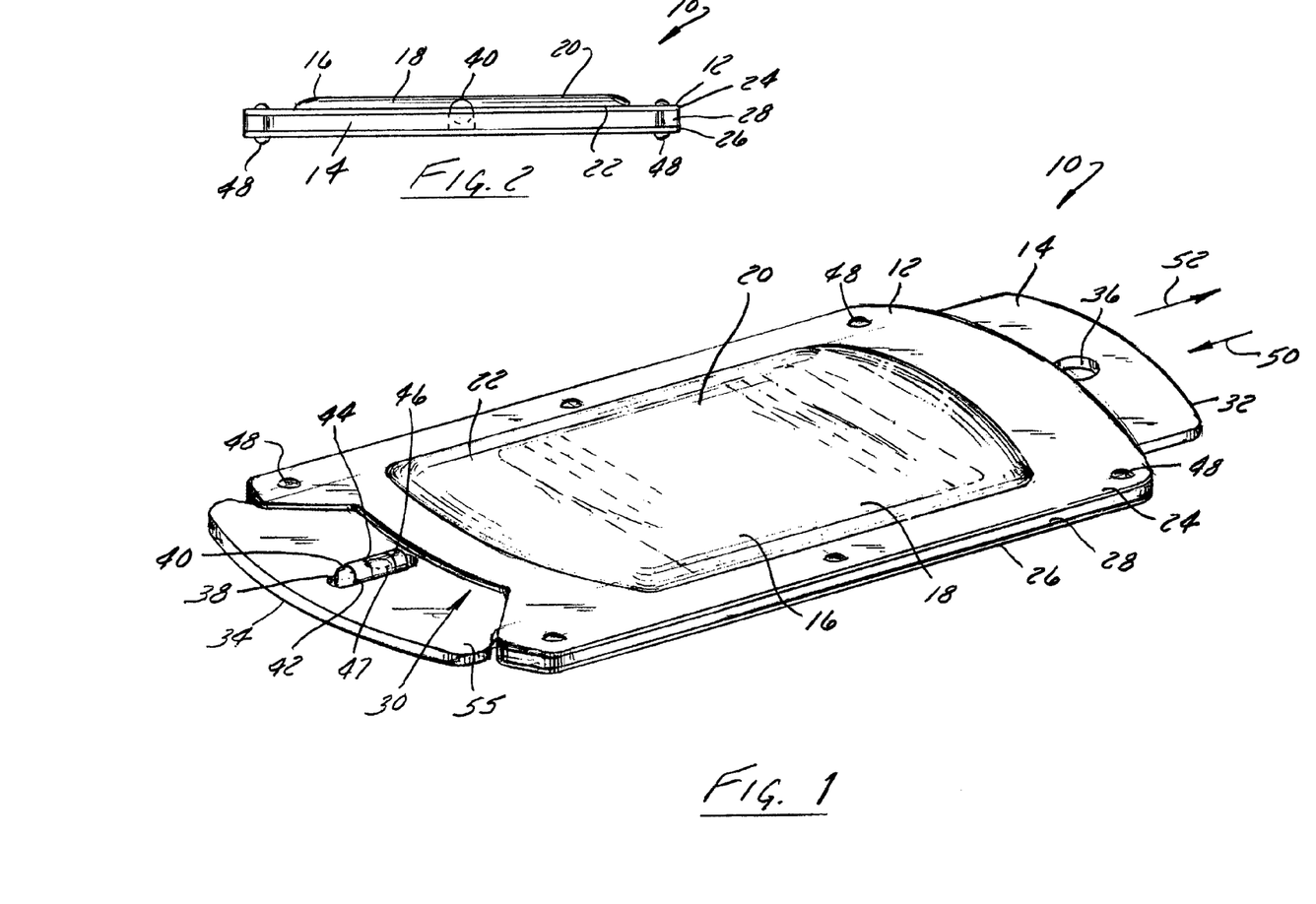
FIG. 1 is a perspective view of a seat sizer according to one embodiment of the invention.
FIG. 2 is a side elevation view of the sizer shown in FIG. 1.

FIGS. 1-5 show a saddle or bicycle seat sizing device, a bicycle seat alignment tool, or sizer 10 according to one embodiment of the present invention. Referring to FIG. 1, sizer 10 includes a first portion, section, or memory portion 12 and a second portion, section, or scale portion 14. Memory portion 12 is movably positionable relative to scale portion 14 to allow registration of the relative positions of the respective portions. Memory portion 12 includes a cavity 16 that encloses a volume of a pliable material 18. Preferably, pliable material 18 is movable and able to maintain a head-height or other relative configuration or shape. One such pliable material is commonly referred to a flowable cushioning media. Examples of such media are disclosed in U.S. Pat. Nos. 5,421,874; 5,549,743; 5,626,657; 6,020,055; and 6,197,099; the disclosures of which are incorporated herein. It is envisioned that pliable material 18 be any material that is displaceable when subjected to loading, reusable for being repeatedly subjected to loading and unloading, and able to maintain a size and shape for a duration of at least 2 seconds after unloading. Preferably, pliable material 18 maintains a particular shape for a duration sufficient to allow a user to disengage from sizer 10 and inspect the area associated with pliable material 18.

Pliable material 18 is enclosed in cavity 16 such that the pliable material 18 can be displaced therein. Cavity 16 is defined by oppositely facing cover surfaces 20, 22. Preferably, cover surfaces 20, 22 are constructed such that when areas of cover surfaces 20, 22 are displaced to be proximate one another, scale portion 14 is visible through cover surfaces 20, 22 when the scale portion is positioned generally behind cavity 16.

As shown in FIG. 1, memory portion 12 includes a top panel 24, a bottom panel 26, and an intermediary member 28 position therebetween. A channel 30 is formed between top panel 24, bottom panel 26, and intermediary member 28 and shaped to slidably receive scale portion 14 therein. Scale portion 14 includes a first end 32 and a second end 34 that each extend beyond channel 30 when the lateral midpoints of scale portion 14 and memory portion 12 are aligned. Ends 32, 34 generally assist in the manipulation of scale portion 14 relative to memory portion 12. First end 32 includes an opening or hole 36 that is shaped to generally receive a user's finger to assist in the efficient registration or alignment of scale portion 14 and memory portion 12. Second end 34 of scale portion 14 also includes an opening 38 constructed to receive an inclination indicator 40 therein. As described below with respect to FIG. 8, inclination indicator 40 assists a user in positioning a bicycle seat relative to a bicycle frame. As shown, inclination indicator 40 is a bubble vile 42 having a number of reference lines 44, 46 that are associated with a bubble 47 to provide an indication of the inclination of indicator 40 with respect to a horizontal reference.

Referring to FIG. 2, sizer 10 includes a number of fasteners 48 which extended generally about the perimeter of sizer 10 and secure top panel 24, bottom panel 26, and intermediary member 28 relative to one another. Cavity 16 extends generally above top panel 24 so as to allow uninterrupted translation of scale portion 14 relative to memory portion 12. Inclination indicator 40 extends generally outward from scale portion 14 such that scale portion 14 is only removable from memory portion 12 in the direction indicated by arrow 50 (FIG. 1). Understandably, inclination indicator 40 could be recessed within a spatial perimeter of scale portion 14 such that scale portion 14 could be positioned relative to memory portion 12 via movement of either scale portion 14 or memory portion 12 in either direction 50, or an opposite direction, indicated by arrow 52 (FIG. 1). Preferably, memory portion 12 and scale portion 14 are completely separable as described further with respect to FIG. 3.

Figure 3:
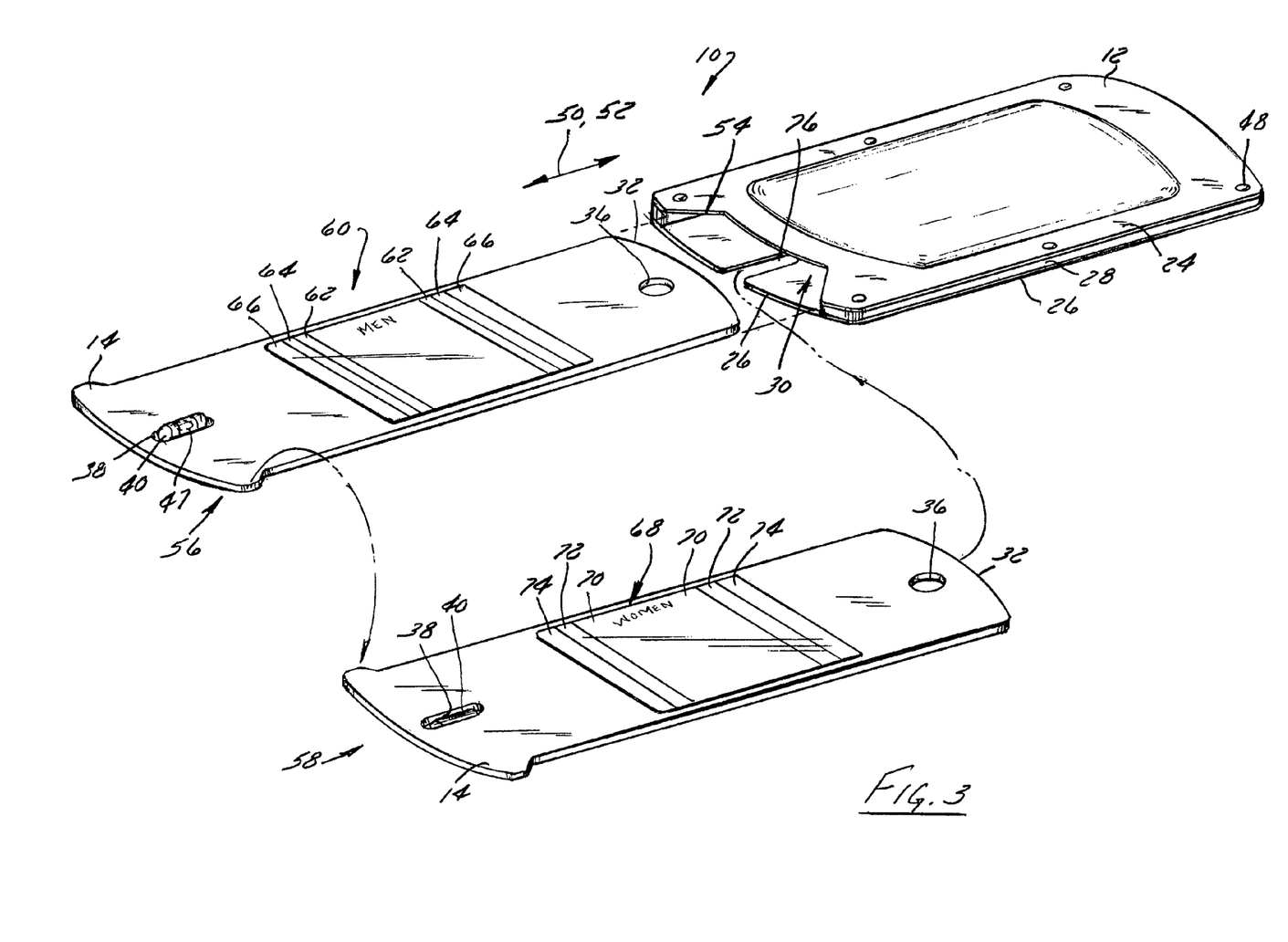
FIG. 3 is a perspective view of the sizer shown in FIG. 1 with a scale portion removed from a memory portion and shown in various orientations in which the scale portion cooperates with the memory portion.

As shown in FIG. 3, scale portion 14 is removable and reversible relative to memory portion 12. Top panel 24 of memory portion 12 includes a recess 54 to provide a gripping surface 55 of scale portion 14 to accommodate a user hands during positioning of scale portion 14 relative to memory portion 12. As shown in FIG. 3, scale portion 14 and memory portion 12 are configured to cooperate with one another with scale portion 14 in either of a first orientation 56 or a second orientation 58. Accordingly, scale portion 14 is engageable with channel 30 of memory portion 12 in more than one position. Scale portion 14 includes a first indicator or scale 60 having a number of indicia 62, 64, 66 that are associated with both an anatomical feature of the user and a device or cycling accessory such as a bicycle seat. Preferably, the anatomical feature is an ischial tuberosity of a rider and indicia 62, 64, 66 are calibrated to average variants of the anatomical feature. More preferably, indicia 62, 64, 66 are calibrated to the average variants of a selected class of user. That is, preferably, indicia 62, 64, 66 are associated with both a gender specific anatomical feature and a product whose shape and size preferably varies as a function of the size of the anatomical feature.

Still referring to FIG. 3, scale portion 14 includes a second indicator or scale 68 that is different than scale 60. Scale 68 also includes a number of indicia 70, 72, 74 that are also associated with an anatomical feature of a user. Preferably, scales 60 and 68 are specific to user classes. More preferably, scale 60 provides an indication of male ischial tuberosity spacing and scale 68 provides an indication of female ischial tuberosity spacing such that sizer 10 can be used to assess the ischial tuberosity spacing of both male and female users. Still more preferably, scales 60, 68 are also associated with a product whose shape and size can vary depending on the anatomical feature and gender of the class associated with the respective scale. Understandably, it is envisioned at scales 60, 68 can be calibrated for use with user classifications other than gender such as, for example, user age, etc. Scale portion 14 is engageable with channel 30 of memory portion 12 when positioned in either of orientation's 56, 58 thereby increasing the functionality of sizer 10 by providing multiple product associated scales that can be registered with respect to the memory portion. Alternatively, it is envisioned that scale portion 14 could be elongated so as to provide multiple product specific scales on a common side thereof such that sizer 10 could be utilized by various classes of users without requiring reorientation of scale portion 14 relative to memory portion 12. It is further envisioned that sizer 10 include scales tailored to other anatomical features and products related thereto, such as feet and shoes, hands and grips, etc., thereby further enhancing the multi-functionality of sizer 10.

Bottom panel 26 of memory portion 12 includes an opening a recess 76 formed therein and positioned generally proximate recess 54 of top panel 24. Recess 76 accommodates inclination indicator 40 when scale portion 14 is introduced into channel 30 in orientation 58. Such accommodating structure increases the range of translation of scale portion 14 relative to memory portion 12 thereby increasing the range of movement available for registering second scale 68 relative to memory portion 12.

Figure 4:
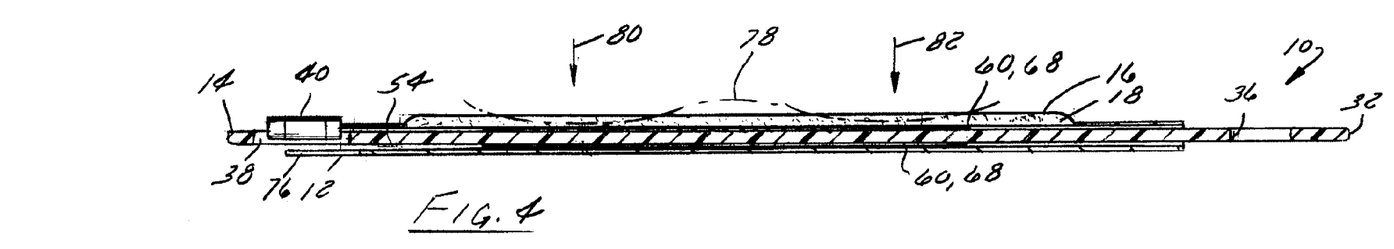
FIG. 4 is a side elevation view showing the sizer of FIG. 1 in use to assess the spacing of the ischial tuberosities of a user.
Figure 5:
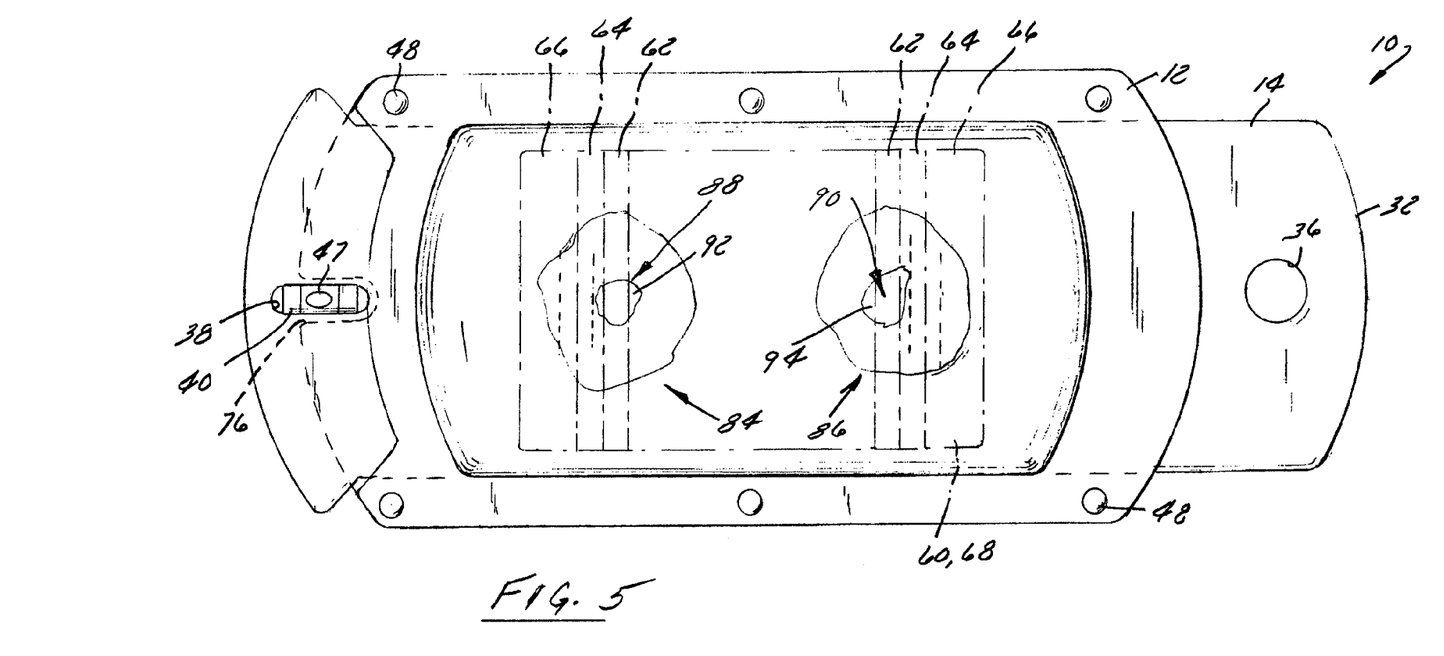
FIG. 5 is a top plan view of the sizer shown in FIG. 1 with the scale portion positioned generally behind the memory portion such that a size indication is visible through a displaceable media of the memory portion.

Referring to FIGS. 4 and 5, during use of sizer 10, a user first selects the appropriate scale 60, 68 based upon the user's class. Scale portion 14 is then slidably positioned relative to memory portion 12 such that the desired scale 60, 68 is oriented to face cavity 16 of pliable material 18. A user 78 intending to determine their ischial tuberosity spacing then sits upon the displaceable material 18 of sizer 10. The downward pressure, indicated by arrows 80, 82, associated with the ischial tuberosities of the user 78 can move the displaceable material 18 from areas 84, 86 (FIG. 5) thereby creating depressions 88, 90 in displaceable material 18 such that portions 92, 94 of scale 60, 68 is visible therebehind. Understandably, if user 78 does not have sufficient weight to fully displace the displaceable material 18 proximate areas 84, 86 such that portions 92, 94 of scale 60, 68 are visible therebehind when the user rises from sizer 10, user 78 may simply manually manipulate depressions 88, 90 such that portions 92, 94 of scale 60, 68 visibility are created in the deepest areas of the depressions 88, 90.

Generally, when user 78 rises from sizer 10, memory portion 12 maintains depressions 88, 90 such that the user may visually inspect scale 60, 68 position therebehind. Having generated visible scale portions 92, 94 in pliable material 18, user 78 or another technician then translates scale portion 14 relative to memory portion 12 to register portions 92, 94 of scale 60, 68 relative to depressions 88, 90 such that generally mirror images of scales 60, 68 are visible through displaceable material 18 are shown in portions 92, 94. The indicia 62, 64, 66, 70, 72, 74 visible through depression 88, 90 when scale portion 14 is registered with memory portion 12 indicate a size and shape of a cycling accessory generally associated with the anatomical feature used to generate depressions 88, 90.

Preferably, indicia 62, 64, 66; 70, 72, 74 are associated with both the user class and a shape and size of a cycling device such that the user can readily determine the appropriately sized device. Preferably, indicia 62, 64, 66; 70, 72, 74 are color-coded and coordinated with a corresponding color-coded schedule and/or packaging associated with the respective cycling device such that the user simply identifies the color that is most abundantly visible through memory portion 12 and selects a seat or other bicycle accessory associated with the corresponding color.

Subsequent users of sizer 10, if portions of scale 60, 68 remain visible through deformable material 18, merely reapportion deformable material 18 within cavity 16 such that scale portion 14 is not visible through the deformable material 18. Preferably, deformable material 18 maintains depressions 88, 90 for a duration sufficient to allow user 78 to inspect the scale portion 14 positioned therebehind. After extended durations, it is envisioned that deformable material 18 will creep to an equalization position wherein memory portion 12 is readily usable. Regardless of the creep and depression maintaining duration of deformable material 18, sizer 10 is reusable and simple to use. The calibration of indicia 62, 64, 66; 70, 72, 74 to both user classes and products associated with the respective scales resolves the potential of subjective interpretation and measurement of the anatomical feature represented in displaceable material 18. That is, as shown in FIG. 5, the symmetrical registration of scale portion 14 relative to memory portion 12 reduces the potential for various interpretations and/or measurements of the spacing between the anatomical features and the determination of the appropriate size of accessory associated therewith. Accordingly, sizer 10 reduces the effects associated with the non-symmetrical and non-repetitive nature of the generation of depressions 88, 90. Registration of scale portion 14 relative to memory portion 12 about a generally central axis and registering indicia 62, 64, 66; 70, 72, 74 relative to a desired size and shape of the accessory and to the class of user enhances the functionality of sizer 10 and provides a sizer that is quick and simple to use.

Figure 6:
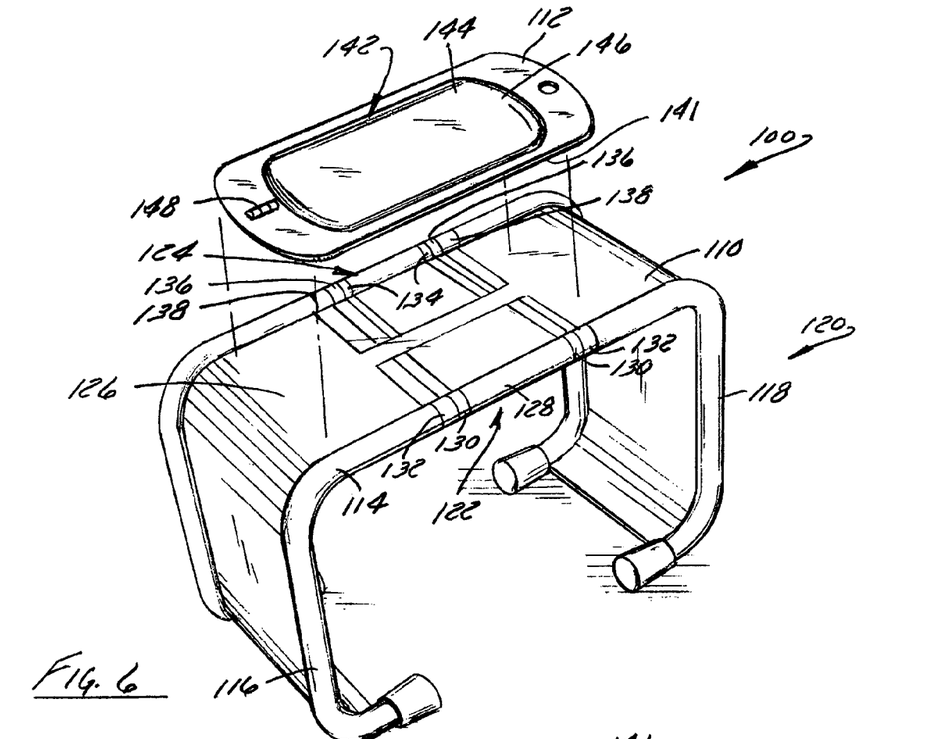
FIG. 6 is a perspective view of a seat sizing tool according to another embodiment of the invention with the scale portion and memory portion separated.
Figure 7:
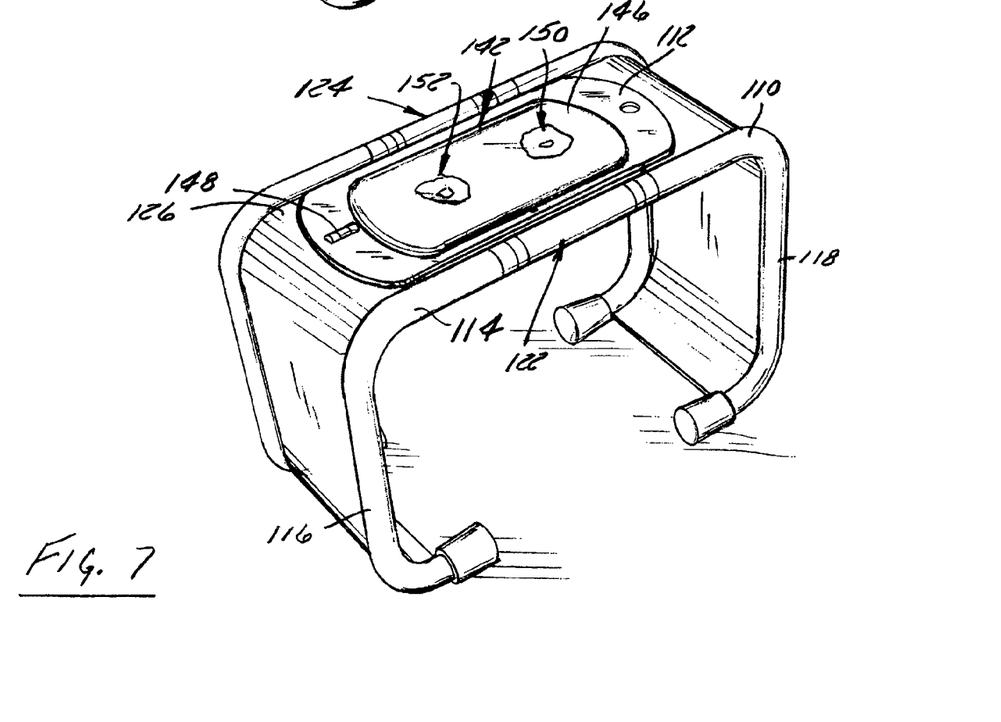
FIG. 7 is a perspective view of the sizer shown in FIG. 6 with the scale portion and the memory portion associated to provide a measurement of an anatomical feature of a user.

FIGS. 6 and 7 show another embodiment of a seat or saddle sizing device, a bicycle or seat tool, or sizer 100 according to the present invention. As shown in FIG. 6, a scale portion 110 is constructed to generally underlie and support a memory portion 112. Scale portion 110 includes a horizontal member 114 elevated by oppositely positioned leg portions 116, 118. Scale portion 110 is provided in a generally seat, stool, or bench 120 shape and is constructed to support a user upon horizontal member 114 such that the user's torso and legs are oriented in a common riding position. Scale portion 110 includes a first scale 122 and a second scale 124 positioned generally opposite first scale 122. Unlike sizer 10, scales 122, 124 of sizer 100 are positioned on a common surface 126 of horizontal member 114. Understandably, sizer 100 could include scales on the top and bottom surfaces of horizontal member 114 provided sizer 100 included legs extending in both directions relative to horizontal member 114.

Each scale 122, 124 includes a number of indicia 128, 130, 132, 134, 136, 138 that are selectively indexed to a class of user and a bicycle accessory or device as described above with respect to sizer 10. Memory portion 112 includes oppositely facing cover members 141, 142 positioned to define a cavity 144 for enclosing a volume of a pliable or deformable material 146. Like material 18, material 146 is movable relative to cavity 144 such that material 146 can be displaced within cavity 144 when subjected to the compressions associated with anatomical features. In inclination indicator 148, such as a bubble vial, is attached to memory portion 112 and is usable for orienting respective bicycle structures, such as a seat to a frame.

Referring to FIG. 7, in use, memory portion 112 is placed upon horizontal member 114 of scale portion 110 or other surface capable of supported a seated user. A user desiring to determine a preferred seat shape and size sits upon deformable material 146 of memory portion 112 thereby creating depressions 150, 152 which will be associated with the spacing of the ischial tuberosities. As described above, if the user's weight is insufficient to generate a depression deep enough such that the respective scale 122, 124 is visible through material 146, the user simply manually manipulates depressions 150, 152 such that scale 122, 124 is visible through material 146. Having generated the viewing windows associated with depressions 150, 152, the user then translates memory portion 112 relative to scale portion 110 so as to register mirror images of indicia 128, 130, 132, 134, 136, 138 within the viewing windows associated with depressions 150, 152. Registration of indicia 128, 130, 132, 134, 136, 138 of the respective scale 122, 124 with the viewable portions of the depressions 150, 152 associates the size of the user's anatomical feature with the appropriately shaped and/or sized accessory or supplemental structure.

Preferably, scales 122, 124 are gender specific and indicia 128, 130, 132, 134, 136, 138 are specific to common ranges of gender specific ischial tuberosity spacing. More preferably, indicia 128, 130, 132, 134, 136, 138 are also directly correlated to a variety of bicycle seat products that are shaped and/or sized to correspond to the gender and the ischial tuberosity spacing of the specific user. Accordingly, both sizer 10 and sizer 100 provide a measuring tool that is simple to use, can be reused, and allows a user to quickly identify those products that are configured to correspond to the physiology of the particular user.

Figure 8:
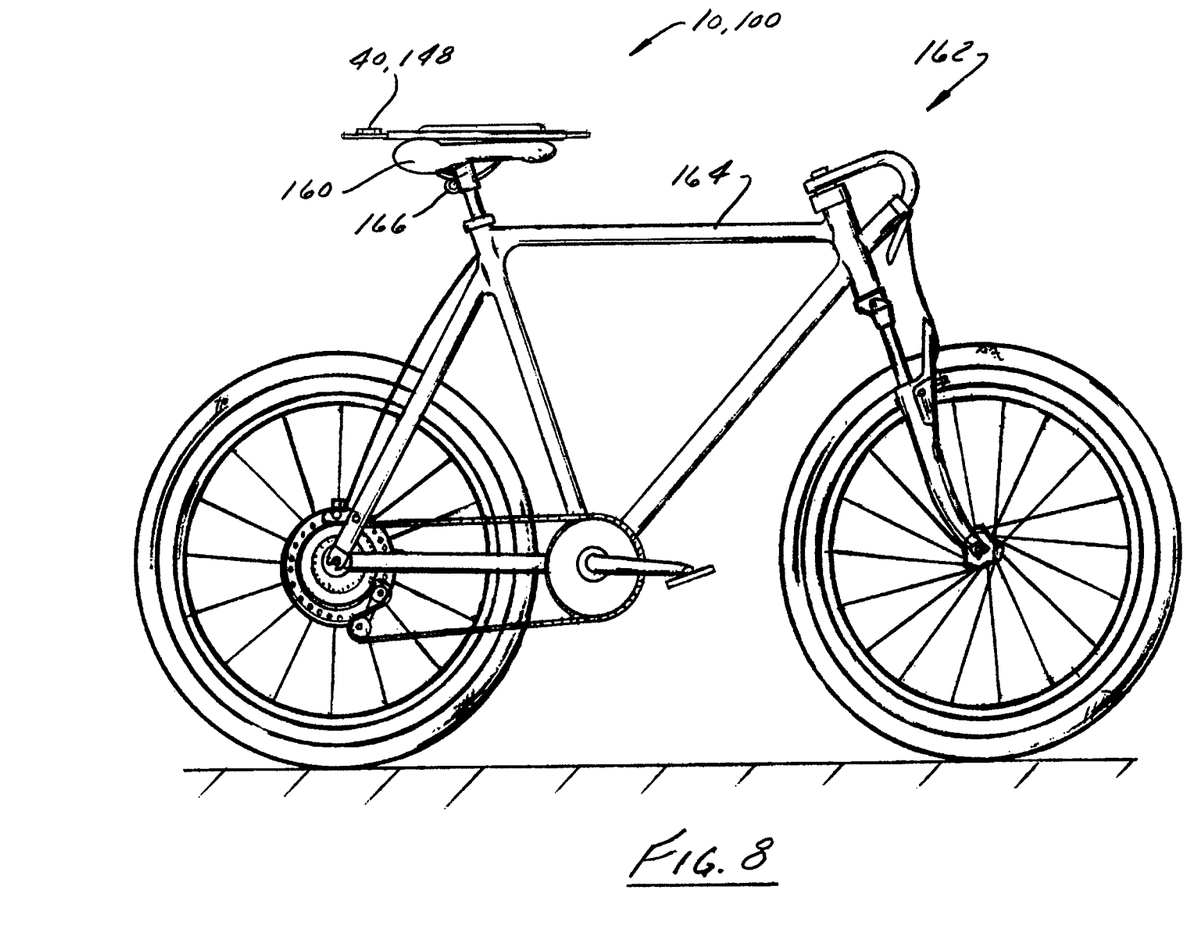
FIG. 8 is a side elevational view of at least a portion of a tool according to either of the embodiments shown in FIGS. 1-5 and FIGS. 6 and 7 with the tool positioned relative to a bicycle seat for orienting the seat relative to a bicycle frame.

FIG. 8 shows another use of sizer 10, 100. As shown in FIG. 8, that portion of sizer 10, 100 equipped with inclination indicator 40, 148 can generally align with a bicycle saddle or seat 160 such that a user or other technician can quickly orient seat 160 with respect to bicycle 162. Improper alignment of seat 160 with bicycle 162 and bicycle frame 164 can offset any comfort achieved by having a properly sized seat. Inclination indicator 40, 148 provides for the efficient and repeatable alignment and/or inclination of seat 160 relative to bicycle 162. As is commonly understood, if bicycle 162 is positioned on a level surface inclination indicator 40, 148 can provide an indication of the inclination of seat 160 relative to bicycle 162. It is further understood that inclination indicator 40, 148 can also provide repeatable indications of inclination beyond simply level orientations. That is, for some classes, genders, ages, or sizes of riders it may be beneficial to maintain a seat to frame orientation that is less than perfectly aligned. Some riders may benefit from inclinations wherein bubble 47 of inclination indicator 40, 148 is closer to, or even overlap, one or another of lines 44, 46.

To adjust the inclination of seat 160 relative to frame 164, a user simply manipulates a pivotable connection 166 that allows inclination of seat 160 relative to frame 164. Visual inspection of inclination indicator 40, 148 provides an indication of the inclination of pitch of seat 160 relative to frame 164. The user then tightens pivotable connection 166 to maintain the desired or preferred orientation of seat 160 relative to frame 164. It is appreciated that although inclination indicator 40, 148 is shown as what is commonly understood as a bubble vial other electronic devices are readily available which provide an indication of inclination in a visual, audible, or tactile modality. That is, such devices commonly beep, illuminate of flash LED's or other light means, or have different vibration rates or intensities that are used to indicate a desired degree of inclination of the device. It is appreciated that any such devices may be integrated into either of sizer 10 of sizer 100 in addition to, or as a replacement for, bubble vial inclination indicator 40, 148. It is further appreciated that sizer 10, 100 may be used to orient other bicycle components, such as handlebars, panniers, lights, rear racks, etc., relative to frame 164 in a horizontally aligned manner.

Sizers 10, 100 further indicate the appreciation that inclination indicator 40, 148 could be attached to either of scale portion 14, as in sizer 10, or memory portion 112, as in sizer 100. Regardless of the relative position and operational methodology of inclination indicator 40, 148 relative to the remaining assemblies of sizers 10, 100, sizers 10, 100 allow for both the association of a specific users anatomy with a preferred seat size as well as the ability to assist in the proper installation of the preferred seat. Accordingly, sizers 10, 100 are easy to use and multifunctional with respect to configuring a bicycle to a particular user.

In accordance with the above, one embodiment of the invention includes a seat sizer having a first member and a second member. The first member includes a cavity having a pliable material contained therein and being displaceable in the cavity. The first and second members are moveable relative to one another and an indicator is connected to the second member. The indicator is configured to be visible through the cavity to indicate a lateral spacing of an anatomical feature.

Another embodiment includes a saddle sizing device having a first portion and a second portion that cooperates with the first portion. The first portion includes an amount of a pliable material affixed thereto. The second portion cooperates with the first portion to bypass the pliable material. A first indicator is attached to the second portion and is configured to correspond to an anatomical feature of a first class of user. A second indicator is attached to the second portion and configured to correspond to an anatomical feature of a second class of user.

Another embodiment can include a bicycle seat tool that has a sizer with a memory portion movably associated with a scale portion. A volume of deformable material is attached to the memory portion and displaceable when subjected to loading. A first scale is attached to the scale portion and has a generally centrally oriented origin. An inclination indicator is attached to one of the memory portion and the scale portion.

Equivalents, alternatives, and modifications, aside from those illustrative embodiments expressly stated, are possible and within the scope of the appending claims. It is further appreciated that the respective features of any one of the embodiments discussed above is not necessarily solely exclusive thereto.

What is claimed is:

1. A seat sizer, comprising:
 a first member including a first transparent surface, a second transparent surface, and a cavity located between the first transparent surface and the second transparent surface;
 a pliable material contained in the cavity and displaceable therein; and
 a second member that is slidably movable relative to the second transparent surface of the first member;
 wherein the second member comprises a first indicator configured to be visible through the first transparent surface, the second transparent surface, and the cavity to indicate a positioning of an anatomical feature such that:
  when the pliable material is displaced in the cavity by compressing the first transparent surface to the second transparent surface, the first indicator is visible through the first member; and
  when the pliable material is not displaced in the cavity, the first indicator is not visible through the first member.

2. The seat sizer of claim 1, wherein the second member further comprises a second indicator.

3. The seat sizer of claim 2, wherein the first indicator and second indicator are located on generally opposite sides of the second member and the second member is rotatable relative to first member.

4. The seat sizer of claim 3, wherein the second member comprises a bench.

5. The seat sizer of claim 2, wherein the indicator is calibrated to a first set of users and the second indicator is calibrated to a second set of users.

6. The seat sizer of claim 5, wherein the first set of users is men and the second set of users is women.

7. The seat sizer of claim 1, wherein the anatomical feature is an ischial tuberosity.

8. The seat sizer of claim 1, further comprising an inclination indicator attached to one of the first member and second member.

9. The seat sizer of claim 1, wherein:
the first transparent surface is flexible and the second transparent surface is rigid; and
the slidably movable second member is configured such that the first indicator can be aligned with the displacement created when the pliable material is displaced in the cavity by compressing the first transparent surface to the second transparent surface.

10. A saddle sizing device, comprising:
a transparent first portion having an amount of a pliable material affixed thereto; and
a second portion cooperating with the transparent first portion and located opposite of the pliable material;
wherein:
the second portion comprises a first indicator configured to correspond to an anatomical feature of a first class of user;
the second portion comprises a second indicator configured to correspond to an anatomical feature of a second class of user; and
the transparent first portion and the second portion are configured such that after depressions are formed in the transparent first portion, the second portion can be registered under the depressions such that:
when depressions are formed in the pliable material, at least one of the first indicator and the second indicator is visible through the transparent first portion; and
when no depressions are formed in the pliable material, the at least one of the first indicator and the second indicator is not visible through the transparent first portion.

11. The saddle sizing device of claim 10, wherein the first and second classes of users are gender specific.

12. The saddle sizing device of claim 10, wherein the first and second indicators are located at generally opposite sides of the second portion.

13. The saddle sizing device of claim 12, wherein the second portion is constructed to alternately engage the first portion in a first orientation, wherein the first indicator faces the pliable material and a second orientation wherein the second indicator faces the pliable material.

14. The saddle sizing device of claim 10, further comprising an inclination indicator for indicating an incline of a saddle relative to a bicycle frame.

15. The saddle sizing device of claim 14, wherein the inclination indicator is a bubble vial.

16. The saddle sizing device of claim 14, wherein the inclination indicator is secured to the first portion.

17. The saddle sizing device of claim 10, wherein the second portion has a horizontal portion and opposite vertical portions, the first and second indicator being positioned along generally opposite edges of the horizontal portion.

18. The saddle sizing device of claim 17, wherein the vertical portions and constructed to elevate the horizontal portion to a sitting height.

19. A bicycle seat tool, comprising:
a sizer including:
a memory portion movably associated with a scale portion in a planar direction;
wherein:
the memory portion comprises a first transparent surface, a second transparent surface, and a volume of deformable material located between the first transparent surface and the second transparent surface and configured to displace when subjected to loading;
the scale portion comprises a first scale; and
the memory portion and the scale portion are configured such that the scale portion can be aligned under displacements formed in the memory portion such that:
when displacements are formed in the memory portion, the first scale is visible through the memory portion; and
when no displacements are formed in the memory portion, the first scale is not visible through the memory portion; and
an inclination indicator tool attached to at least one of the memory portion and the scale portion.

20. The bicycle seat tool of claim 19, wherein the scale portion further comprises a second scale.

21. The bicycle seat tool of claim 20, wherein the first scale and the second scale are one of positioned on opposite facing sides of the scale portion and laterally spaced from one another on a common side of the scale portion.

22. The bicycle seat tool of claim 21, wherein the scale portion forms a seat having a generally planar seating surface.

23. The bicycle seat tool of claim 20, wherein the first scale is associated with an anatomical feature of men and the second scale is associated with the same anatomical feature of women.

24. The bicycle seat tool of claim 19, wherein the sizer further comprises a slot configured to receive the scale, and the slot extends along the second transparent surface.

25. The bicycle seat tool of claim 19, wherein the first scale includes a number of colored areas that extend from a centrally oriented origin.

* * * * *